United States Patent [19]

Narva et al.

[11] Patent Number: 5,186,934
[45] Date of Patent: Feb. 16, 1993

[54] *BACILLUS THURINGIENSIS* GENE ENCODING A COLEOPTERAN-ACTIVE TOXIN

[75] Inventors: Kenneth E. Narva, San Diego; George E. Schwab, La Jolla; Gregory A. Bradfisch, San Diego, all of Calif.

[73] Assignee: Mycogen Corporation, San Diego, Calif.

[21] Appl. No.: 715,184

[22] Filed: Jun. 12, 1991

Related U.S. Application Data

[63] Continuation-in-part of Ser. No. 658,935, Feb. 21, 1991, abandoned.

[51] Int. Cl.$^5$ .................. A01N 63/00; C12N 1/21; C12N 1/15; C12N 15/32
[52] U.S. Cl. .................. 124/93 A; 435/252.3; 435/252.31; 435/252.34; 435/254; 435/69.1; 435/320.1; 435/255; 435/240.4; 536/23.71; 530/350; 800/205
[58] Field of Search .................. 530/350; 536/27; 435/69.1, 71.2, 91, 172.1, 172.3, 252.3, 320.1; 935/6, 9, 10, 22, 33, 59, 60, 61, 66, 72; 424/93

[56] References Cited

U.S. PATENT DOCUMENTS

| | | | |
|---|---|---|---|
| 4,448,885 | 5/1984 | Schnepf et al. | 435/252.33 |
| 4,467,036 | 8/1984 | Schnepf et al. | 435/320.1 |
| 4,771,131 | 9/1988 | Herrnstadt et al. | 536/27 |
| 4,849,217 | 7/1989 | Soares et al. | 424/93 L |
| 4,996,155 | 2/1991 | Sick et al. | 435/252.3 |

FOREIGN PATENT DOCUMENTS 0202739  3/1986  European Pat. Off. .

OTHER PUBLICATIONS

Schnepf, H. Ernest and H. R. Whitely (1981) Cloning and Expression of the *Bacillus thuringiensis* Crystal Gene in *E. coli*. Proc. Natl. Acad. Sci. USA vol. 78, No. 5, pp. 2893-2897.
Thorne et al., 1986, J. Bacteriol., 166(3): 801-811.

*Primary Examiner*—Richard A. Schwartz
*Assistant Examiner*—Nancy T. Vogel
*Attorney, Agent, or Firm*—Saliwanchik & Saliwanchik

[57] ABSTRACT

A novel *B.t.* gene encoding a toxin which is toxic to coleopteran insects has been cloned from a coleopteran-active *B. thuringiensis* microbe. The DNA encoding the *B.t.* toxin can be used to transform various prokaryotic and eukaryotic microbes to express the *B.t.* toxin. These recombinant microbes can be used to control coleopteran insects in various environments.

25 Claims, 1 Drawing Sheet

5,186,934

BACILLUS THURINGIENSIS GENE ENCODING A COLEOPTERAN-ACTIVE TOXIN

CROSS-REFERENCE TO A RELATED APPLICATION

This is a continuation-in-part of co-pending application Ser. No. 07/658,935, filed on Feb. 21, 1991 now abandoned.

BACKGROUND OF THE INVENTION

The most widely used microbial pesticides are derived from the bacterium Bacillus thuringiensis. This bacterial agent is used to control a wide range of leafeating caterpillars, Japanese beetles and mosquitos. Bacillus thuringiensis produces a proteinaceous paraspore or crystal which is toxic upon ingestion by a susceptible insect host. For example, B. thuringiensis var. kurstaki HD-1 produces a crystal called a delta endotoxin which is toxic to the larvae of a number of lepidopteran insects. The cloning and expression of this B.t. crystal protein gene in Escherichia coli has been described in the published literature (Schnepf, H. E. and Whitely, H. R. [1981] Proc. Natl. Acad. Sci. USA 78:2893-2897). U.S. Pat. No. 4,448,885 and U.S. Pat. No. 4,467,036 both disclose the expression of B.t. crystal protein in E. coli. European Patent Application, Publication No. 0 202 739, discloses a novel B. thuringiensis microbe which can be used to control coleopteran pests in various environments. U.S. Pat. No. 4,849,217 discloses Bacillus thuringiensis isolates active against the alfalfa weevil. One of the isolates disclosed is B. thuringiensis PS86A1 (NRRL B-18400).

BRIEF SUMMARY OF THE INVENTION

Disclosed and claimed is a novel toxin gene which expresses a novel toxin toxic to coleopteran insects. This toxin gene can be transferred to suitable hosts via plasmid vector.

Specifically, the invention comprises a novel delta endotoxin gene which encodes an approximately 58 kDa protein, as determined by SDS-PAGE analysis, which has the DNA sequence shown in Sequence ID No. 3. Also embodied within the invention is the novel toxin having the amino acid sequence shown in Sequence ID No. 4

BRIEF DESCRIPTION OF THE SEQUENCES

Figure 1:
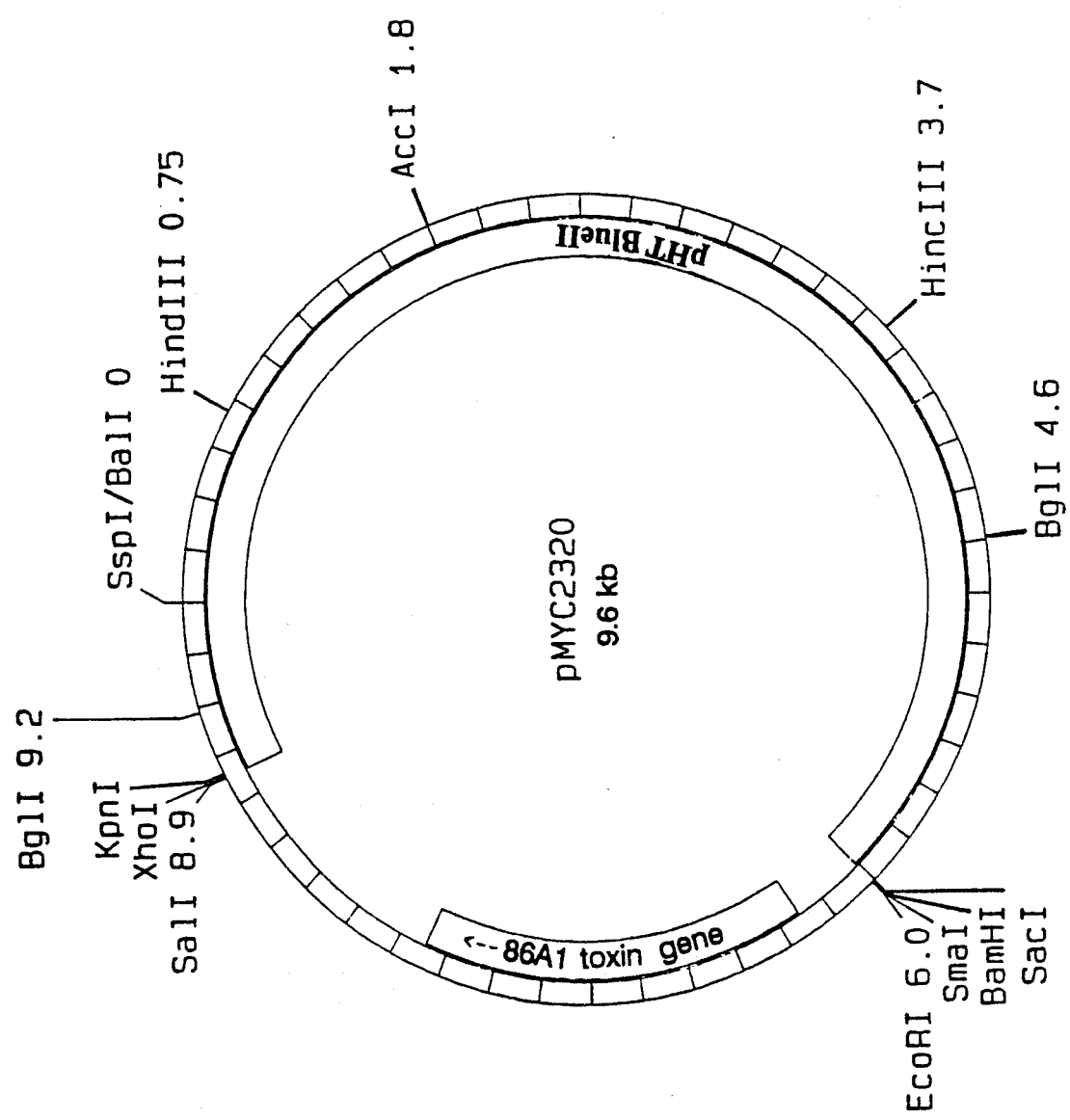
FIG. 1 - Restriction map of plasmid pMYC2320.

Sequence ID No. 1 - Gene 86A1-A probe
Sequence ID No. 2 - N-terminal amino acid sequence
Sequence ID No. 3 - DNA sequence of novel gene.
Sequence ID No. 4 - Amino acid sequence of novel toxin.

DETAILED DISCLOSURE OF THE INVENTION

The novel toxin gene of the subject invention was obtained from a novel coleopteran-active B. thuringiensis (B.t.) isolate designated PS86A1.

B. thuringiensis isolate PS86A1, NRRL B-18400, can be cultured using standard known media and fermentation techniques. Upon completion of the fermentation cycle, the bacteria can be harvested by first separating the B.t. spores and crystals from the fermentation broth by means well known in the art.

Subcultures of B.t. isolate PS86A1 and the E. coli host harboring the toxin gene of the invention, E. coli NM522(pMYC2320) were deposited in the permanent collection of the Northern Research Laboratory, U.S. Department of Agriculture, Peoria, Ill., USA. The accession numbers are as follows:

| Culture | Accession Number | Deposit Date |
| --- | --- | --- |
| B.t. isolate PS86A1 | NRRL B-18400 | August 16, 1988 |
| E. coli NM522(pMYC2320) | NRRL B-18769 | February 14, 1991 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The toxin gene of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of coleopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., general Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus, and Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A wide variety of ways are available for introducing the *B.t.* gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5′ to 3′ direction of the coding or sense sequence, the construct will involve the transcriptional regulatory region, if any, and the promoter, where the regulatory region may be either 5′ or 3′ of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarin et al., (1981) Gene 16:237, and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and-positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B.t.i. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis*, and the like.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the coleopteran pest(s), e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

EXAMPLE 1

Purification of a Novel Coleopteran-Active Toxin From *Bacillus thuringiensis* Strain PS86A1

The *Bacillus thuringiensis* (B.t.) isolate PS86A1 was cultured in a medium comprised of the following:

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| pH 7.2 | |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | 3.66 g |
| $CaCl_2.2H_2O$ | |

The salts solution and $CaCl_2$ solution are filter-sterilized and added to the autoclaved broth at the time of inoculation. Flasks are incubated at 30° C. on a rotary shaker at 200 rpm for ca. 64 hr. The parasporal inclusion bodies, spores, and cellular debris were collected by centrifugation (7.14 k*g*20 min.). The parasporal inclusion bodies were partially purified by sodium bromide (28-38%) isopycnic gradient centrifugation (M.A. Pfannenstiel et al. [1984] FEMS Microbiol. Lett. 21:39). The partially purified protein toxic to the Egyptian alfalfa weevil, *Hypera brunneipennis*, was bound to the Immobilon-P, PVDF membrane (Millipore, Bedford, Mass.) by western blotting techniques (H. Towbin et al. [1979] Proc. Natl. Acad. Sci. USA 76:4350). The N-terminal amino acid sequence was determined by the standard Edman reaction with an automated gas-phase sequenator (M. W. Hunkapiller et al. [1983] Meth. Enzymol. 91:399). The sequence obtained was as follows:

$NH_2$—MIIDSKTTLPRHSLIHTIKL—$CO_2H$

From this sequence, the following oligonucleotide probe was designed:

5'ATGATTGATTCTAAAACAACATTAC-
CAAGACATTCT/A
TTAATT/ACATACT/AATT/AAA3'

EXAMPLE 2

Molecular Cloning of Gene Encoding a Novel Toxin from *Bacillus thuringiensis* Strain PS86A1

Total cellular DNA was prepared from PS86A1 cells grown to an optical density, at 600 nm, of 1.0. Cells were pelleted by centrifugation and resuspended in protoplast buffer (20 mg/ml lysozyme in 0.3M sucrose, 25 mM Tris-Cl, pH 8.0, 25 mM EDTA). After incubation at 37° C. for 1 hour, protoplasts were lysed by two cycles of freezing and thawing. Nine volumes of a solution of 0.1M NaCl, 0.1% SDS, 0.1M Tris-Cl were added to complete lysis. The cleared lysate was extracted twice with phenol:chloroform (1:1). Nucleic acids were precipitated with two volumes of ethanol and pelleted by centrifugation. The pellet was resuspended in 10 mM Tris-Cl, 1 mM EDTA (TE), pH 8.0, and RNAse was added to a final concentration of 50 μg/ml. After incubation at 37° C. for 1 hour, the solution was extracted once each with phenol:chloroform (1:1) and TE-saturated chloroform. DNA was precipitated from the aqueous phase by the addition of one-tenth volume of 3M NaOAc and two volumes of ethanol. DNA was pelleted by centrifugation, washed with 70% ethanol, dried, and resuspended in TE.

Restriction fragment length polymorphism (RFLP) analyses were performed by standard hybridization of southern blots of PS86A1 DNA with a $^{32}$P-labeled oligonucleotide probe designated as 86A1-A. The sequence of the 86A1-A probe was:

5'ATGATTGATTCTAAAACAACATTAC-
CAAGACATTCT/A
TTAATT/ACATACT/AATT/AAA3'

The probe was mixed at four positions, as shown. Hybridizing bands included an approximately 3.6 kbp HindIII fragment and an approximately 9.3 kbp EcoRV fragment.

A gene library was constructed from PS86A1 DNA partially digested with Sau3A. Partial restriction digests were fractionated by agarose gel electrophoresis. DNA fragments 6.6 to 23 kbp in size were excised from the gel, electroeluted from the gel slice, and recovered by ethanol precipitation after purification on an ElutipD ion exchange column. The Sau3A inserts were ligated into BamHI-digested LambdaGem-11 (Promega, Madison, Wis.). Recombinant phage were packaged and plated on *E. coli* KW251 cells (Promega). Plaques were screened by hybridization with the radiolabeled 86A1-A oligonucleotide probe. Hybridizing phage were plaque-purified and used to infect liquid cultures of *E. coli* KW251 cells for isolation of phage DNA by standard procedures (Maniatis et al. [1982] *Molecular Cloning: A Laboratory Manual*, Cold Spring Harbor Laboratory, Cold Spring Harbor, N.Y.). For subcloning, preparative amounts of DNA were digested with EcoRI and SalI, and electrophoresed on an agarose gel. The approximately 2.9 kbp band containing the toxin gene was excised from the gel, electroeluted from the gel slice, and purified by ion exchange chromatography as above. The purified DNA insert was ligated into EcoRI+SalI-digested pHTBlueII (an *E. coli*/B.t. shuttle vector comprised of pBlueScript S/K (Stratagene, San Diego, Calif.) and the replication origin from a resident B.t. plasmid (D. Lereclus et al. [1989] FEMS Microbiol. Lett. 60:211-218). The ligation mix was used to transform frozen, competent *E. coli* NM522 cells (ATCC 47000). Transformants were plated on LB agar (Maniatis et al., supra) containing ampicillin, isopropyl-($\beta$)-D-thiogalactoside (IPTG), and 5-bromo-4-chloro-3-indolyl-($\beta$)-D-galactoside (XGAL). Plasmids were purified from putative recombinants by alkaline lysis (Maniatis et al., supra) and analyzed by electrophoresis of EcoRI and SalI digests on agarose gels. The desired plasmid construct, pMYC2320, contains the novel toxin gene of the invention. See FIG. 1. The DNA sequence of this gene is shown in Sequence ID No. 1. The novel toxin expressed by this gene is shown in Sequence ID No. 2.

Plasmid pMYC2320 was introduced into an acrystalliferous (Cry−) *B.t.* host (B.t. HD-1 Cry B, A. I. Aronson, Purdue University, West Lafayette, Ind.) by electroporation. Expression of an approximately 58 kDa protein is verified by SDSPAGE analysis and activity against the alfalfa weevil.

The restriction enzymes disclosed herein can be purchased from Bethesda Research Laboratories, Gaithersburg, Md., or New England Biolabs, Beverly, Mass. The enzymes are used according to the instructions provided by the supplier.

Plasmid pMYC2320 containing the *B.t.* toxin gene, can be removed from the transformed host microbe by use of standard well-known procedures. For example, *E. coli* NM522(pMYC2320) can be subjected to cleared lysate isopycnic density gradient procedures, and the like, to recover pMYC2320.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A = adenine
G = guanine
C = cytosine
T = thymine
X = T or C if Y is A or G
X = C if Y is C or T
Y = A, G, C or T if X is C
Y = A or G if X is T
W = C or A if Z is A or G
W − C if Z is C or T
Z = A, G, C or T if W is C
Z = A or G if W is A
QR = TC if S is A, G, C or T; alternatively QR = AG if S is T or C
J = A or G
K = T or C
L = A, T, C or G
M = A, C or T The above shows that the novel amino acid sequences of the *B.t.* toxins can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249-255). Thus, the subject invention includes mutants of the amino acid sequence depicted herein which do not alter the protein secondary structure, or if the structure is altered, the biological activity is retained to some degree.

EXAMPLE 3

Insertion of Toxin Gene Into Plants

The novel gene coding for the novel coleopteran-active toxin, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983] Cell 32:1033-1043). A particularly useful vector in this regard is pEND4K (Klee, H. J., Yanofsky, M. F. and Nester, E. W. [1985] Bio/Technology 3:637-642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 4

Cloning of Novel *Bacillus thuringiensis* Gene Into Baculoviruses

The novel gene of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399-406), and pAC380, described by Smith et al. (Smith, G. E., Summers, M. D. and Fraser, M. J. [1983] Mol Cell. Biol. 3:2156-2165). The gene coding for the novel protein toxin of the invention can be modified with BamHI linkers at appropriate regions both upstream and downstream from the coding region and inserted into the passenger site of one of the AcNPV vectors.

EXAMPLE 5

Toxicity of Purified Protein from the Isolate PS86A1 and Purified Toxin Expressed in B.t. HD-1 Cry B Host to Egyptian Alfalfa Weevil, *Hypera brunneipennis*

Fifty microliters of 2 mg/ml purified protein was pipetted onto 1 ml of artificial diet in wells of a standard 24-well bioassay plate. One first or second instar larva was added to each well.

Assays were graded for mortality 6 days post-treatment. Larvae which did not respond to prodding with a dull probe were considered dead. Experiments were replicated on successive days. Toxicity is shown below (Table 1).

TABLE 1

Toxicity of purified protein to the Egyptian alfalfa weevil, *Hypera brunneipennis*

| Source of protein | Mean Percent Mortality |
|---|---|
| PS86A1 | 46.8 |
| Expression in *B.t.* HD-1 Cry B | 61.5 |
| Untreated | 2.0 |

EXAMPLE 6

Growth Inhibition by Purified Toxin Expressed in B.t. HD-1 Cry B Host to Western Spotted Cucumber Beetle, *Diabrotica undecimpunctata undecimpunctata*

One hundred microliters of a 2 mg/ml aqueous suspension of purified toxin was pipetted onto 1 ml of an artificial diet in wells of a standard 24-well assay plate. One first instar *D.u. undecimpunctata* larva was added to each well.

Growth was measured by weighing larva at the end of an 8-day assay period. Growth reduction (G.R.) was determined according to the formula:

$$G.R. = (1 - T/C) * 100$$

where, C=average mass of control larvae (mg) and, T=average mass of treated larvae (mg).

Experiments were replicated on separated days. Purified toxin reduced the rate of growth of *D.u. undecimpunctata* by 36.6 percent relative to untreated controls.

EXAMPLE 7

The novel toxin of the invention when expressed in a *B.t.* HD-1 Cry B host is also active against other *Hypera* spp., for example, *H. meles* (clover head weevil), *H. nigrirostris* (lesser clover leaf weevil), *H. postica* (alfalfa weevil), and *H. punctata* (clover leaf weevil).

---

We claim:

1. A purified DNA encoding an ≈58 kDa *Bacillus thuringiensis* toxin active against coleopteran pest, said DNA having the DNA sequence shown in Sequence ID No. 3.

2. Essentially pure toxin active against coleopteran pests, said toxin having the amino acid sequence shown in Sequence ID No. 4.

3. A recombinant DNA transfer vector comprising DNA which codes for a toxin active against coleopteran pests, said toxin having the amino acid sequence shown in Sequence ID No. 4.

4. The DNA transfer vector, according to claim 3, transferred to and replicated in a prokaryotic or lower eukaryotic host.

5. A microorganism transformed to express a *Bacillus thuringiensis* toxin as defined in claim 2.

6. *Escherichia coli* NM522(pMYC2320), having the identifying characteristics of NRRL B-18769.

7. The microorganism, according to claim 5, which is a species of Pseudomonas, Bacillus, Azotobacter, Erwinia, Serratia, Klebsiella, Rhizobium, Rhodopseudomonas, Methylophilius, Agrobacterium, Acetobacter or Alcaligenes.

8. The microorganism, according to claim 7, wherein said microorganism is pigmented and phylloplane adherent.

9. A method for controlling an insect from the genus Hypera which comprises administering to said pest or to the environment of said pest a microorganism according to claim 7.

10. The method, according to claim 9, wherein said administration is to the rhizosphere.

11. The method, according to claim 10, wherein said administration is to the phylloplane.

12. The method, according to claim 9, wherein said administration is to a body of water.

13. The method, according to claim 9, wherein said Hypera spp. is *Hypera brunneipennis* (Egyptian alfalfa weevil).

14. The method, according to claim 9, wherein said Hypera spp. is selected from the group consisting of *H. meles* (clover head weevil), *H. nigrirostris* (lesser clover leaf weevil), *H. postica* (alfalfa weevil), and *H. punctata* (clover leaf weevil).

15. An insecticidal composition comprising insecticide containing substantially intact, treated cells having prolonged pesticidal activity when applied to the environment of a target pest, wherein said insecticide is a polypeptide toxic to coleopteran insects, is intracellular, and is produced as a result of expression of a transformed microbe capable of expressing the *Bacillus thuringiensis* toxin as defined in claim 2.

16. The insecticidal composition, according to claim 15, wherein said treated cells are treated by chemical or physical means to prolong the insecticidal activity in the environment.

17. The insecticidal composition, according to claim 16, wherein said cells are prokaryotes or lower eukaryotes.

18. The insecticidal composition, according to claim 17, wherein said prokaryotic cells are selected from the group consisting of Enterobacteriaceae, Bacillaceae, Rhizobiaceae, Spirillaceae, Lactobacillaceae, Pseudomonadaceae, Azotobacteraceae, and Nitrobacteraceae.

19. The insecticidal composition, according to claim 17, wherein said lower eukaryotic cells are selected from the group consisting of Phycomycetes, Ascomycetes, and Basidiomycetes.

20. The insecticidal composition, according to claim 15, wherein said cell is a pigmented bacterium, yeast, or fungus.

21. The insecticidal composition, according to claim 15, wherein said coleopteran insect is the Egyptian alfalfa weevil.

22. Treated, substantially intact unicellular microorganism cells containing an intracellular toxin, which toxin is a result of expression of a *Bacillus thuringiensis* toxin gene toxic to coleopteran insects which codes for a polypeptide toxin as defined in claim 2, wherein said cells are treated under conditions which prolong the insecticidal activity when said cell is applied to the environment of a target insect.

23. The cells, according to claim 22, wherein the cells are treated by chemical or physical means to prolong the insecticidal activity in the environment.

24. The cells according to claim 22, wherein said coleopteran insect is the alfalfa weevil.

25. Plasmid denoted pMYC2320.

UNITED STATES PATENT AND TRADEMARK OFFICE
CERTIFICATE OF CORRECTION

PATENT NO. : 5,186,934
DATED : February 16, 1993
INVENTOR(S) : Kenneth E. Narva, et. al.

It is certified that error appears in the above-indentified patent and that said Letters Patent is hereby corrected as shown below:

On the Title page, item [57], col. 2,

Abstract   line 3: "B. thurningiensis" should read --B. thuringiensis--.

Column 3   line 7: "general" should read --genera--.

Column 5   line 4: "Bagdasarin" should read --Bagdasarian--.

Column 7   line 39: "3.66 g" should be moved to the next line.

Signed and Sealed this

Twenty-first Day of December, 1993

Attest:

BRUCE LEHMAN

Attesting Officer        Commissioner of Patents and Trademarks

SEQUENCE LISTING ( 1 ) GENERAL INFORMATION:

( i i i ) NUMBER OF SEQUENCES: 4

( v i ) CURRENT APPLICATION DATA:
        (A) APPLICATION NUMBER: 07/715,184
        (B) FILING DATE: JUN. 12, 1991

( 2 ) INFORMATION FOR SEQ ID NO:1:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Bacillus thuringiensis
        ( B ) STRAIN: PS86A1

( x i ) SEQUENCE DESCRIPTION: SEQ ID NO:1:

```
ATGATTGATT  CTAAAACAAC  ATTACCAAGA  CATTCWTTAA  TWCATACWAT    5 0
WAA                                                           5 3
```

( 3 ) INFORMATION FOR SEQ ID NO:2:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Bacillus thuringiensis
        ( B ) STRAIN: PS86A1

( x i ) SEQUENCE DESCRIPTION: SEQ ID NO:2:

-continued

Met Ile Ile Asp Ser Lys Thr Thr Leu Pro Arg His Ser Leu Ile His
1 5 10 15

Thr Ile Lys Leu
20

( 4 ) INFORMATION FOR SEQ ID NO:3:

( i ) SEQUENCE CHARACTERISTICS:
( A ) LENGTH: 1425 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: BACILLUS THURINGIENSIS
( C ) INDIVIDUAL ISOLATE: PS86A1

( v i i ) IMMEDIATE SOURCE:
( A ) LIBRARY: LAMBDAGEM (TM) - 11 LIBRARY OF KENNETH NARVA
( B ) CLONE: PS86A1-A ( i x ) FEATURE:
( A ) NAME/KEY: matpeptide
( B ) LOCATION: 1..1425

( x i ) SEQUENCE DESCRIPTION: SEQ ID NO:3:

```
ATGATTATTG ATAGTAAAAC GACTTTACCT AGACATTCAC TTATTCATAC AATTAAATTA     60
AATTCTAATA AGAAATATGG TCCTGGTGAT ATGACTAATG GAAATCAATT TATTATTTCA    120
AAACAAGAAT GGGCTACGAT TGGAGCATAT ATTCAGACTG GATTAGGTTT ACCAGTAAAT    180
GAACAACAAT TAAGAACACA TGTTAATTTA AGTCAGGATA TATCAATACC TAGTGATTTT    240
TCTCAATTAT ATGATGTTTA TTGTTCTGAT AAAACTTCAG CAGAATGGTG GAATAAAAAT    300
TTATATCCTT TAATTATTAA ATCTGCTAAT GATATTGCTT CATATGGTTT TAAAGTTGCT    360
GGTGATCCTT CTATTAAGAA AGATGGATAT TTTAAAAAAT TGCAAGATGA ATTAGATAAT    420
ATTGTTGATA ATAATTCCGA TGATGATGCA ATAGCTAAAG CTATTAAAGA TTTTAAAGCG    480
CGATGTGGTA TTTTAATTAA AGAAGCTAAA CAATATGAAG AAGCTGCAAA AAATATTGTA    540
ACATCTTTAG ATCAATTTTT ACATGGTGAT CAGAAAAAAT TAGAAGGTGT TATCAATATT    600
CAAAAACGTT TAAAAGAAGT TCAAACAGCT CTTAATCAAG CCCATGGGGA AAGTAGTCCA    660
GCTCATAAAG AGTTATTAGA AAAAGTAAAA AATTTAAAAA CAACATTAGA AAGGACTATT    720
AAAGCTGAAC AAGATTTAGA GAAAAAAGTA GAATATAGTT TTCTATTAGG ACCATTGTTA    780
GGATTTGTTG TTTATGAAAT TCTTGAAAAT ACTGCTGTTC AGCATATAAA AAATCAAATT    840
GATGAGATAA AGAAACAATT AGATTCTGCT CAGCATGATT TGGATAGAGA TGTTAAAATT    900
ATAGGAATGT TAAATAGTAT TAATACAGAT ATTGATAATT TATATAGTCA AGGACAAGAA    960
GCAATTAAAG TTTTCCAAAA GTTACAAGGT ATTTGGGCTA CTATTGGAGC TCAAATAGAA   1020
AATCTTAGAA CAACGTCGTT ACAAGAAGTT CAAGATTCTG ATGATGCTGA TGAGATACAA   1080
ATTGAACTTG AGGACGCTTC TGATGCTTGG TTAGTTGTGG CTCAAGAAGC TCGTGATTTT   1140
ACACTAAATG CTTATTCAAC TAATAGTAGA CAAAATTTAC CGATTAATGT TATATCAGAT   1200
TCATGTAATT GTTCAACAAC AAATATGACA TCAAATCAAT ACAGTAATCC AACAACAAAT   1260
ATGACATCAA ATCAATATAT GATTTCACAT GAATATACAA GTTTACCAAA TAATTTTATG   1320
TTATCAAGAA ATAGTAATTT AGAATATAAA TGTCCTGAAA ATAATTTTAT GATATATTGG   1380
TATAATAATT CGGATTGGTA TAATAATTCG GATTGGTATA ATAAT                   1425
```

( 5 ) INFORMATION FOR SEQ ID NO:4:

( i ) SEQUENCE CHARACTERISTICS:
        ( A ) LENGTH: 475 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: BACILLUS THURINGIENSIS
        ( C ) INDIVIDUAL ISOLATE: PS86A1

( i x ) FEATURE:
( A ) NAME/KEY: Protein
( B ) LOCATION: 1..475

( x i ) SEQUENCE DESCRIPTION: SEQ ID NO:4:

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300
```

| | | | | | | | | | | | | | |
|---|---|---|---|---|---|---|---|---|---|---|---|---|---|
| Asn | Ser | Ile | Asn | Thr | Asp | Ile | Asp | Asn | Leu | Tyr | Ser | Gln | Gly | Gln | Glu |
| 305 | | | | 310 | | | | 315 | | | | | | | 320 |
| Ala | Ile | Lys | Val | Phe | Gln | Lys | Leu | Gln | Gly | Ile | Trp | Ala | Thr | Ile | Gly |
| | | | | 325 | | | | | 330 | | | | | 335 | |
| Ala | Gln | Ile | Glu | Asn | Leu | Arg | Thr | Thr | Ser | Leu | Gln | Glu | Val | Gln | Asp |
| | | | 340 | | | | | 345 | | | | | 350 | | |
| Ser | Asp | Asp | Ala | Asp | Glu | Ile | Gln | Ile | Glu | Leu | Glu | Asp | Ala | Ser | Asp |
| | | 355 | | | | | 360 | | | | | 365 | | | |
| Ala | Trp | Leu | Val | Val | Ala | Gln | Glu | Ala | Arg | Asp | Phe | Thr | Leu | Asn | Ala |
| | 370 | | | | | 375 | | | | | 380 | | | | |
| Tyr | Ser | Thr | Asn | Ser | Arg | Gln | Asn | Leu | Pro | Ile | Asn | Val | Ile | Ser | Asp |
| 385 | | | | | 390 | | | | | 395 | | | | | 400 |
| Ser | Cys | Asn | Cys | Ser | Thr | Thr | Asn | Met | Thr | Ser | Asn | Gln | Tyr | Ser | Asn |
| | | | | 405 | | | | | 410 | | | | | 415 | |
| Pro | Thr | Thr | Asn | Met | Thr | Ser | Asn | Gln | Tyr | Met | Ile | Ser | His | Glu | Tyr |
| | | | 420 | | | | | 425 | | | | | 430 | | |
| Thr | Ser | Leu | Pro | Asn | Asn | Phe | Met | Leu | Ser | Arg | Asn | Ser | Asn | Leu | Glu |
| | | 435 | | | | 440 | | | | | | 445 | | | |
| Tyr | Lys | Cys | Pro | Glu | Asn | Asn | Phe | Met | Ile | Tyr | Trp | Tyr | Asn | Asn | Ser |
| | 450 | | | | | 455 | | | | | 460 | | | | |
| Asp | Trp | Tyr | Asn | Asn | Ser | Asp | Trp | Tyr | Asn | Asn | | | | | |
| 465 | | | | | 470 | | | | | 475 | | | | | |